United States Patent [19]

Sofranko et al.

[11] 4,450,293

[45] May 22, 1984

[54] PREPARATION OF α-HYDROXYISOBUTYRIC ACID USING A THALLIC HALIDE CATALYST

[75] Inventors: John A. Sofranko, West Chester; John J. Leonard, Springfield, both of Pa.

[73] Assignee: Atlantic Richfield Company, Los Angeles, Calif.

[21] Appl. No.: 449,300

[22] Filed: Dec. 13, 1982

[51] Int. Cl.$^3$ .............................................. C07C 59/00
[52] U.S. Cl. .................................................. 562/579
[58] Field of Search ......................... 562/579; 568/910

[56] References Cited

U.S. PATENT DOCUMENTS 2,971,981  2/1961  Aries ................................... 562/579
3,198,823  8/1965  Akabayashi et al. ............... 562/579
3,284,494  11/1966  Schoenbrunn ...................... 568/910

FOREIGN PATENT DOCUMENTS 470216  12/1950  Canada ................................ 568/910

Primary Examiner—Paul J. Killos
Attorney, Agent, or Firm—Delbert E. McCaslin

[57] ABSTRACT

A process for the preparation of α-hydroxyisobutyric acid by the catalytic oxidation of isobutyric acid with oxygen in an aqueous solution in the presence of a $TlCl_3$ or $TlBr_3$ catalyst and a Cu, Sn, or Fe halide compound as a redox agent. Optionally alkali metal halides may be employed to promote catalysis and control the halide concentration.

14 Claims, No Drawings

PREPARATION OF α-HYDROXYISOBUTYRIC ACID USING A THALLIC HALIDE CATALYST

BACKGROUND OF THE INVENTION

Alpha-hydroxyisobutyric acid has been prepared by oxidizing an aqueous solution of the corresponding alcohol in the presence of a base and a platinum catalyst as shown for example in C. K. Heyns and H. Paulsen, "Newer Methods of Preparative Organic Chemistry" Vol. II, pp. 303 (1963).

As described in an article by E. F. Schoenbrunn and J. H. Gardner, J. Am. Chem. Soc., Vol. 82, pp. 4905 (1960) and U.S. Pat. Nos. 2,847,453, 2,847,454 and 2,847,465 α-hydroxyisobutyric acid may be produced by the liquid phase oxidation of isobutylene with nitrogen tetroxide and nitric acid.

An article by E. C. Taylor, H. W. Artland and G. McGillivray, Tetrahedron Letters, No. 60, pp. 5285–5288 (1970) discloses the preparation of for example, α-isobutoxyiso-butyric acid using thallium (III) acetate with an excess of neat isobutyric acid to prepare a thallium (III) carboxylate and acetic acid with removal of the acetic acid by distillation and reflux under nitrogen of the thallium (III) carboxylate in an isobutyric acid solvent to give the α-acyloxycarboxylic acid.

U.S. Pat. No. 3,897,489 discloses a method for the production of alpha-hydroxyisobutyric acid by the catalytic oxidation of isobutylene glycol with molecular oxygen in the presence of a supported platinum catalyst.

The process of the present invention provides a high yield selectivity to the α-hydroxyisobutyric acid by the liquid phase catalytic oxidation of isobutyric acid with a TlCl$_3$ or TlBr$_3$ catalyst and a metal halide redox agent. Isobutyric acid is readily available from the oxidation of isobutyraldehyde obtained for example as a by-product in n-butyraldehyde/n-butanol production.

The α-hydroxyisobutyric acid product of this invention may be dehydrated to methacrylic acid by known methods, as shown for example in U.S. Pat. No. 3,562,320 (1971), or reacted with methanol to give methyl methacrylate directly as described in British Pat. No. 852,664.

SUMMARY OF THE INVENTION

According to the present invention there is provided an improved oxidation process for the preparation of α-hydroxyisobutyric acid by reacting in the aqueous phase isobutyric acid and oxygen in the presence of a TlCl$_3$ or TlBr$_3$ salt and a Cu, Sn or Fe halide compound as a redox agent and optionally an alkali metal halide to promote catalysis and control halide concentration.

It is an object of this invention to provide an improved process for the preparation of alpha-hydoxyisobutyric acid by the catalyst oxidation of isobutyric acid.

It is another object of this invention to provide a novel reaction system useful in the conversion of isobutyric acid to α-hydroxyisobutyric acid.

A further object is to provide a specific mechanism for the employment of a thallium (III) chloride or bromide and a metal halide redox agent in an oxidation process for preparing α-hydroxyisobutyric acid.

These and other objects and advantages of this invention will become apparent from the description of the invention which follows and from the claims.

DESCRIPTION OF THE INVENTION

In accordance with this invention, alpha-hydroxyisobutyric acid is produced by the catalytic oxidation of isobutyric acid with molecular oxygen in an aqueous solution at temperatures of from about 75° C. to 250° C. and preferably 125° C. to 200° C. in the presence of a thallic chloride or thallic bromide catalyst and a catalytic amount of a copper, iron or tin halide as a co-oxidant redox catalyst. Optionally an alkali metal halide may be employed to promote catalysis and control and maintain the halide concentration of the reaction system.

A general postulated equation for the reaction may be represented as follows:

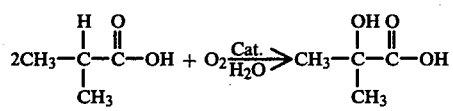

The reaction between the isobutyric acid and oxygen may be carried out in an autoclave or any other high pressure reactor. A general procedure is to charge the isobutyric acid as a water solution or thallic catalyst, Cu, Fe or Sn co-oxidant redox catalyst and optionally an alkali metal halide into the reactor vessel which may be sealed and pressurized with air or oxygen, which may be diluted with other gases such as nitrogen, argon or other gases and then heated to the desired temperature with stirring for the desired time. The reaction may be carried out batchwise or as a continuous process and the order of addition of the reactants and catalyst may be varied to suit the particular apparatus employed. At the end of the reaction period the reaction product α-hydroxyisobutyric acid is recovered and treated by any conventional method such as filtration, etc. to effect separation of insoluble catalyst and components formed by the reaction.

The oxidation is carried out in the aqueous phase with the isobutyric acid concentration in the aqueous solution ranging from 5 weight percent of 75 weight percent with between 10 and 50 weight percent being preferred. The isobutyric acid employed which may for example be obtained by the oxidation of isobutyraldehyde should be relatively pure and not contain any appreciable amounts of contaminants such as n-butanol, butyric acid, etc. which would affect the reaction and make recovery of product α-hydroxyisobutyric acid difficult.

The thallic chloride or thallic bromide catalyst employed in the process of this invention in amounts of from about 0.1 to 10 weight percent preferably from 1 to 5 weight percent may be in a homogeneous state in the reaction mixture at reaction conditions. Thus, the compounds may be present in solution or suspension and may also be on support materials such as alumina, silica gel, zeolites, activated carbon, etc.

The co-oxidant halide salt compounds which may be employed in amounts of from about 0.1 to 10 weight percent preferably 1 to 5 weight percent in the process of the invention include the Cu$^{+1}$, Cu$^{+2}$, Sn$^{+2}$, Sn$^{+4}$ and Fe$^{+2}$, Fe$^{+3}$ halide salts such as copper (I) chloride, copper (I) bromide, copper (II) chloride and bromide, tin (II) chloride and bromide, iron (II) chloride and bromide and iron (III) chloride and bromide tin (IV) chloride and bromide. As with the thallic catalyst the co-oxidant halide may be supported.

As mentioned hereinabove, optionally an alkali metal halide in amounts of from abut 0 to 20 weight percent preferably 1 to 10 weight percent, may be employed in the process of the invention in the catalytic mixture and thereby promote catalysis and assist in controlling halide concentration in the reaction. The alkali metal halides suitable for use include for example sodium chloride, sodium bromide, lithium chloride, lithium bromide, potassium chloride, potassium bromide, etc.

At least stoichiometric amounts of molecular oxygen are employed at oxygen partial pressures of from about 1 to 500 psig. The source of oxygen may be in the form of pure oxygen or preferably an oxygen-containing gas such as air or oxygen diluted with other gases such as nitrogen, argon and the like. The oxygen partial pressure should be such that the explosive range or flammability hazards are avoided. Thus, the concentrations of oxygen should be low enough so that the reaction mixture is not potentially explosive. When the source of oxygen is air the air pressure may be in the range of from about 1 atmosphere to 2500 psig.

Although an aqueous solution is preferably employed in the process, certain organic solvents which contain no functional group oxidizable in the reaction such as sulfolane or diphenyl ether may be used as a cosolvent with water.

Reaction time is generally dependent upon the temperature, pressure and on the amount and type of catalyst and co-oxidant and alkali metal halide, if any, being charged as well as the type of equipment being employed. Usually between 1 hour and 4 hours at reaction temperatures and pressures are required to obtain the desired degree of reaction but shorter or longer reaction times may be employed. Reaction times will vary dependent on whether the process is continuous or batch.

The following examples are provided to illustrate the invention in accordance with the principles of this invention but are not to be construed as limiting the invention in any way except as indicated by the appended claims.

EXAMPLES 1-8

In Examples 1-8 which follow in Table form, an aqueous solution of isobutyric acid, thallic salt, co-oxidant redox catalyst, and alkali metal salt, if any, was charged to a 500 ml titanium autoclave equipped with a magnedrive stirrer, coils for regulating the temperature and a gas inlet for air or oxygen-containing gas mixtures. The autoclave was sealed, heated to the desired temperature with stirring and pressurized with air. At the end of the reaction period, the autoclave was cooled, depressurized and the contents filtered to remove any insoluble catalyst components. The filtrate was analyzed by high pressure liquid chromatography to give the mole percent isobutyric acid (IBA) converted and mole percent yield of product α-hydroxyisobutyric acid (HIBA). IBA converted is the mols of IBA reacted divided by moles of IBA employed and HIBA yield is equal to mols of HIBA formed divided by the mols of IBA reacted.

TABLE

| Ex. No. | Air Pressure (psig) | Thallic Catalyst (wt. %) | Co-oxidant Catalyst (wt. %) | Alkali Metal Halide (wt. %) | IBA (wt. %) | Temp. (°C.) | Time (hrs.) | IBA Converted (mol %) | HIBA Yield (mol %) |
|---|---|---|---|---|---|---|---|---|---|
| 1 | 150 | TlCl$_3$ (2.5) | CuCl$_2$ (1) | NaCl (10) | 10 | 150 | 4 | 24 | 35 |
| 2 | 150 | TlCl$_3$ (2.5) | CuCl$_2$ (1) | NaCl (10) | 10 | 150 | 6 | 30 | 14 |
| 3 | 500 | TlCl$_3$ (2.5) | CuCl$_2$ (1) | NaCl (10) | 10 | 130 | 4 | 22 | 33 |
| 4 | 150 | TlCl$_3$ (2.5) | SnCl$_2$ (1) | LiCl (10) | 15 | 150 | 4 | 27 | 32 |
| 5 | 150 | TlCl$_3$ (2.0) | FeCl$_3$ (1) | KCl (5) | 43 | 150 | 4 | 7 | 35 |
| 6 | 200 | TlBr$_3$ (4.0) | CuBr$_2$ (1) | NaBr (2) | 20 | 150 | 4 | 10 | 31 |
| 7 | 150 | TlCr$_3$ (2.5) | CuCl$_2$ (1) | 0 | 10 | 150 | 4 | 18 | 27 |
| 8 | 200 | TlBr$_3$ (4.0) | CuBr$_2$ (1) | 0 | 10 | 150 | 4 | 9 | 26 |

We claim:

1. A process for the preparation of α-hydroxyisobutyric acid which comprises reacting in an aqueous solution isobutyric acid with molecular oxygen at partial pressures of between about 1 psig to 500 psig and at a temperature in the range of about 75° C. to 250° C. in the presence of a catalyst mixture of
   (a) from about 0.1 to 10 weight percent of a Tl$^{+3}$ halide salt selected from thallic chloride and thallic bromide, or mixtures thereof,
   (b) from 0.1 to 10 weight percent of a copper (I), copper (II), tin (II), tin (IV), iron (II) or iron (III) bromide or chloride co-oxidant salt or mixtures thereof, and recovering the desired α-hydroxyisobutyric acid.

2. A process according to claim 1 wherein the source of oxygen is air which is employed at a total pressure of from about 15 psig to 2500 psig.

3. A process according to claim 1 wherein the reaction temperature is in the range of from 125° C. to 200° C.

4. A process according to claim 1 wherein the Tl$^{+3}$ salt is thallic chloride.

5. A process according to claim 1 wherein the co-oxidant salt is copper (II) chloride.

6. A process according to claim 1 wherein the cooxidant salt is iron (III) chloride.

7. A process according to claim 1 wherein the isobutyric acid is employed in aqueous solution in concentration of from about 5 weight percent to 75 weight percent.

8. A process according to claim 7 wherein the concentration is between 10 and 50 weight percent.

9. A process according to claim 1 wherein the reaction is carried out in the presence of from 0 to 20 weight percent of an alkali metal chloride or bromide as a catalyst promoter.

10. A process according to claim 9 wherein the alkali metal chloride is sodium chloride, lithium chloride, or potassium chloride.

11. A process according to claim 1 wherein the $Tl^{+3}$ halide salt and the co-oxidant salt is employed in amounts of from 1 to 5 weight percent.

12. A process for the preparation of α-hydroxyisobutyric acid which comprises reacting in aqueous solution isobutyric acid with oxygen in the form of air at a total pressure of between about 15 psig and 2500 psig and a temperature of from 125° C. to 200° C. in the presence of a catalyst mixture comprising from 1 to 5 weight percent thallic chloride and from 1 to 5 weight percent copper (II) chloride.

13. A process according to claim 12 wherein the reaction is carried out in the presence of between 1 and 10 weight percent sodium chloride as a catalyst promoter.

14. A process according to claim 1 wherein the $Tl^{+3}$ halide and Cu, Sn or Fe co-oxidant salt are supported.

* * * * *